United States Patent [19]

Mitra

[11] Patent Number: 5,378,785
[45] Date of Patent: Jan. 3, 1995

[54] CEMENTS FROM β-DICARBONYL POLYMERS

[75] Inventor: Sumita B. Mitra, West St. Paul, Minn.

[73] Assignee: Minnesota Mining and Manufacturing Company, St. Paul, Minn.

[21] Appl. No.: 29,124

[22] Filed: Mar. 10, 1993

Related U.S. Application Data

[62] Division of Ser. No. 843,420, Feb. 27, 1992, Pat. No. 5,227,413.

[51] Int. Cl.$^6$ .................. C08F 16/36; C08F 216/36; C08F 220/10; A61K 6/08
[52] U.S. Cl. .................. 526/316; 526/317.1; 526/318; 526/318.4; 526/318.5; 526/273; 526/278; 526/287; 526/239; 526/310; 526/332; 523/115; 523/116
[58] Field of Search .............. 526/316, 317.1, 318, 526/318.2, 318.3, 318.4, 318.5, 273, 274, 278, 286, 332, 239, 287, 310; 523/115, 116

[56] References Cited

U.S. PATENT DOCUMENTS

| | | | |
|---|---|---|---|
| 2,856,418 | 10/1958 | Calvin | 260/429.1 |
| 3,448,089 | 6/1969 | Celeste | 260/78.5 |
| 3,459,790 | 8/1969 | Smith | 260/483 |
| 3,607,834 | 9/1971 | Marx et al. | 526/310 |
| 3,655,605 | 4/1972 | Smith | 260/29.6 |
| 3,736,872 | 6/1973 | Martens et al. | 101/462 |
| 3,814,717 | 6/1974 | Wilson et al. | 260/29.6 |
| 3,855,379 | 12/1974 | Araki et al. | 260/77.5 |
| 3,872,047 | 3/1975 | Jandourek | 260/33.4 |
| 3,954,475 | 3/1976 | Bonham et al. | 96/67 |
| 4,011,201 | 3/1977 | Ponticello | 526/316 |
| 4,015,980 | 4/1977 | MacKay et al. | 75/120 |
| 4,016,124 | 4/1977 | Crisp et al. | 260/29.6 |
| 4,035,321 | 7/1977 | Shahidi et al. | 260/22 |
| 4,077,820 | 3/1978 | Bolza et al. | 149/109.4 |
| 4,089,830 | 3/1978 | Tezuka et al. | 260/29.6 H |
| 4,118,375 | 10/1978 | Lindner et al. | 526/240 |
| 4,143,018 | 3/1979 | Crisp et al. | 260/29.6 |
| 4,144,208 | 3/1979 | Fuchs et al. | 260/27 |
| 4,209,434 | 6/1980 | Wilson et al. | 260/29.6 H |
| 4,212,970 | 7/1980 | Iwasaki | 542/455 |
| 4,288,511 | 9/1981 | Myers et al. | 430/17 |
| 4,296,226 | 10/1981 | Braun et al. | 526/316 |
| 4,317,681 | 3/1982 | Beede et al. | 106/85 |
| 4,342,677 | 8/1982 | Muramatou et al. | 523/116 |
| 4,360,605 | 11/1982 | Schmitt et al. | 523/116 |
| 4,374,936 | 2/1983 | Tomioka et al. | 523/116 |
| 4,376,835 | 3/1983 | Schmitt et al. | 523/116 |
| 4,408,018 | 10/1983 | Bartman et al. | 525/300 |
| 4,438,278 | 3/1984 | Ponticello et al. | 526/310 |
| 4,719,149 | 1/1988 | Aasen et al. | 428/473 |
| 4,732,943 | 3/1988 | Beech et al. | 525/303 |
| 4,746,686 | 3/1988 | Waller | 522/14 |
| 4,758,612 | 7/1988 | Wilson et al. | 524/5 |
| 4,806,381 | 2/1989 | Engelbrecht et al. | 427/2 |
| 4,813,876 | 3/1989 | Wang | 433/224 |

(List continued on next page.)

FOREIGN PATENT DOCUMENTS 0227454 12/1986 European Pat. Off. .
0313387 4/1987 European Pat. Off. .
0323120 12/1988 European Pat. Off. .

(List continued on next page.)

OTHER PUBLICATIONS

Prosser et al., "Litho-ionomer Cements and Their Technological Applications", *J. Chem. Tech. Biotechnol.*, vol. 29, pp. 69–87 (1979).

(List continued on next page.)

*Primary Examiner*—Tae H. Yoon
*Attorney, Agent, or Firm*—Gary L. Griswold; Walter N. Kirn; F. Andrew Ubel

[57] ABSTRACT

The invention provides novel ionomer polymers and cements comprising β-dicarbonyl groups. The invention has particular utility as filling materials for restoring teeth and for cementing inlays and crowns into place in the tooth, providing a base or a lining in a tooth cavity, and as adhesives or sealants. The invention provides ionomer cement systems that achieve increased resistance to water absorption and solubility.

19 Claims, No Drawings

U.S. PATENT DOCUMENTS

| | | | |
|---|---|---|---|
| 4,855,215 | 8/1989 | Nakano et al. | 430/283 |
| 4,872,936 | 10/1989 | Engelbrecht | 156/307.3 |
| 5,017,649 | 5/1991 | Clemens | 525/59 |
| 5,155,252 | 10/1992 | Yamamoto et al. | 526/316 |
| 5,171,763 | 12/1992 | Ohno et al. | 523/116 |
| 5,204,383 | 4/1993 | Manabe et al. | 526/273 |

FOREIGN PATENT DOCUMENTS

| | | |
|---|---|---|
| 2213157 | 8/1989 | United Kingdom. |
| PCT/US93/00380 | 5/1993 | WIPO. |

OTHER PUBLICATIONS

Prosser et al., "Polyelectrolyte Cements", Wilson and Prosser, eds., *Developments in Ionic Polymers*–1, Chapter 5, Applied Science Publishers (London and New York, 1983).

Jensen et al., "Polymerization Shrinkage and Microleakage", Vanherle and Smith, eds., *Posterior Composite Resin Dental Restorative Materials*, pp. 243–5, Peter Szulc Publishing Co. (Netherlands, 1985).

CEMENTS FROM β-DICARBONYL POLYMERS

This is a division of application Ser. No. 07/843,420 filed Feb. 27, 1992, now U.S. Pat. No. 5,227,413.

TECHNICAL FIELD

This invention relates to ionomers, as well as to methods of using such ionomers, and cements formed with such ionomers.

BACKGROUND ART

The materials known as dental ionomer cements have many applications in dentistry including use as filling materials for restoring teeth and for cementing inlays and crowns into place in the tooth, providing a base or a lining in a tooth cavity, and as adhesives or sealants. An ionomer cement is formed by reacting 1) an ionomer polymer with 2) a reactive glass. This reaction is typically done in water.

Ionomer polymers traditionally have been copolymers of two or more monomers. For example, iraconic acid and acrylic acid have often been copolymerized to form such an ionomer polymer. The polymer is formed by reacting the two monomers together using a free radical polymerization mechanism. The ionomer polymer is called such because of its inherent acidity resulting from the numerous acid pendant groups.

After the polymer is made it is often dissolved in water for later mixing with the reactive glass. The reactive glass used in the ionomer cement is often an ion-leachable glass, such as those based on calcium aluminosilicate glasses, or more recently, borate glasses. For a general discussion, see Prosser et at., Polyelectrolyte Cements, Wilson and Prosser, eds., Developments in Ionic Polymers—1, Chapter 5, Applied Science Publishers (London and New York, 1983). The glass is finely ground into a powder to facilitate mixing with the ionomer polymer solution.

In the setting reaction, the glass powder behaves like a base and reacts with the acidic polyelectrolyte, i.e., ionomer polymer, releasing metal ions to form a metal polysalt which acts as the binding matrix. Water serves as the reaction medium and allows the transport of ions in what is essentially an ionic reaction. The setting reaction is therefore characterized as a chemical cure system that proceeds automatically upon mixing the ionomer polymer and glass powder in the presence of water. The cements set to a gel-like state within a few minutes and rapidly harden to develop strength. See, e.g., Prosser et al., J. Chem. Tech. Biotechnol., 29, 69-87 (1979).

Chelating agents, such as tartaric acid, have been described as useful for modifying the rate of setting, e.g., to provide longer working times for the cements. See, e.g., U.S. Pat. Nos. 4,089,830, 4,209,434, 4,317,681, 4,374,936, and 4,758,612. Longer working times afford the dentist more time to mix the cement and apply the cement to the tooth. Unfortunately, when working times are lengthened by the usual methods, setting times are generally also lengthened. A longer setting time decreases the efficiency of the dentist and increases the amount of time the patient must spend in the dental chair. The role of tartaric acid has been explained as involving the temporary withholding of cations from crosslinking the polyanion chains (i.e., the ionomer) through complex formation. See generally, Prosser et at., Polyelectrolyte Cements, supra at Chapter 5.

Many commercially available glass ionomer cements include such chelating agents, and as a result are characterized by working times that are on the order of 1 to 2 minutes, but relatively long setting times, e.g., on the order of 4 to 15 minutes. During this set time the cement must be protected from being washed away by moisture from the mouth (e.g., through the use of cotton pads) but also must not be allowed to dry out. Such conditions can lead to discomfort for the patient as well as the added burden of having to spend extra time in the dentist's chair. Thus present day glass ionomer cements, although beneficial clinically, are quite technique-sensitive, as well as time-consuming for the dentist and patient.

Recently a photocurable ionomer cement has become available commercially. This cement system can provide a long working time and can be cured on demand by exposure to an appropriate source of radiant energy. This cement system is described in European Patent Application No. 0 323 120 and is commercially available as Vitrebond TM Light Cure Glass Ionomer Liner/Base (available from 3M Company, St. Paul, Minn. 55144).

The final set cement must be both durable against frictional wear and resistant to degradation by an aqueous environment. Unfortunately, current ionomer cement systems frequently do not adequately resist degradation when exposed to water and may over time be undesirably eroded away.

SUMMARY OF THE INVENTION

Further adjustability of water miscibility and water absorption would be desirable in order to provide greater flexibility in the formulation of glass ionomer cement systems. Such adjustability is also desirable in order to extend the practical application of such cement systems to uses involving greater exposure of the hardened cement to aqueous environments (e.g., the exposed margin around crowns, sealant surfaces, or exposed restoratives) than is prudently accomplished using current techniques and materials.

The present invention relates to novel ionomer polymers comprising pendent complexing groups, wherein at least one of the pendent complexing groups is β-dicarbonyl group. These polymers are useful in forming dental ionomer cements, dental adhesives or sealants.

The present invention provides, in another aspect, ionomer cement systems that achieve increased resistance to water absorption and solubility. These systems are prepared using ionomers which comprise a polymer having sufficient pendent complexing groups, wherein at least one of the pendent complexing groups on the polymer is a β-dicarbonyl group, to undergo a setting reaction in the presence of a reactive glass powder and water.

The present invention provides, in another aspect, ionomer cement systems that are optionally free-radically or cationically crosslinkable and achieve increased resistance to water absorption and solubility. These systems are prepared using crosslinkable ionomers which comprise a polymer having sufficient pendent complexing groups, wherein at least one of the pendent complexing groups is a β-dicarbonyl group, to undergo a setting reaction in the presence of a reactive glass powder and water, and sufficient pendent polymerizable groups to enable the resulting mixture to be crosslinked by exposure to radiant energy or by a free-radical or cationic mechanism.

The invention also provides methods for preparing and methods for using such ionomer cement systems.

The ionomer cement system of the present invention comprises (a) an ionomer polymer comprising at least one pendent β-dicarbonyl group, and (b) a reactive glass powder. Presently preferred optional ingredients of the crosslinkable ionomer system include water (present in a form that does not prematurely begin to set the system), appropriate polymerization initiators, modifying agents, and copolymerizable and non-copolymerizable cosolvents. Other optional ingredients include pigments, fillers (e.g., pulverized precious or nonprecious metals, silica, quartz or metal oxides), and the like.

The crosslinkable ionomer cement systems of the present invention can be prepared by combining the crosslinkable ionomer and the reactive glass powder in the presence of water. As with present day cement systems, the water serves as a reaction medium allowing the transport of ions between the ionomer and the reactive powder, thereby allowing the acid-base chemical cure "setting" reaction to occur. This setting reaction can also be termed the "cement reaction" in that it will proceed regardless of the co-existing free-radical or cationic mechanism.

The cured systems of the present invention have been found to provide increased resistance to degradation by saliva and other aqueous environments. As a result, the cement surfaces can be exposed to aqueous environments without the need for a separate layer of varnish, glaze, or dental restorative. This feature is particularly beneficial near the margins of crowns and bridges since it is often not practical to varnish or cover these surfaces. While previous ionomer cements have been susceptible to erosion at these margin surfaces to an undesirable degree, the present invention substantially resists such erosion and has greater longevity. Moreover, by the use of fluoride-containing reactive glass powders, as explained more fully below, the present invention provides the ability to prepare a dental restorative that is both crosslinkable and capable of exhibiting cariostatic fluoride release. Such a combination of properties is highly desirable.

The present invention relates to ionomer cement systems useful, for instance, for the preparation of dental and medical adhesives, bases, liners, luting agents, sealants, and filling materials for restorative and/or endodontic use.

DETAILED DESCRIPTION OF THE PRESENTLY PREFERRED EMBODIMENTS

The term "crosslinkable ionomer", as used herein, refers to a polymer having sufficient pendent complexing groups to undergo a setting reaction in the presence of a reactive powder and water, and sufficient pendent polymerizable groups to enable the resulting mixture to be polymerized, i.e., crosslinked, upon exposure to radiant energy, or via a redox or cationic reaction.

The terms "reactive powder" or "reactive glass powder", as used herein, refer to a metal oxide or hydroxide, mineral silicate, or ion-leachable glass that is capable of reacting with the ionomer in the presence of water to form a hydrogel.

The term "ionomer cement system", as used herein, refers to the unmixed, or mixed but unset and uncured, combination of ionomer, reactive powder, and other optional ingredients, such as water. Such systems include kits in which the ionomer is employed as a concentrated aqueous solution, for mixing directly with the powder, as well as kits in which the ionomer is employed in a dry blend with the powder, for later mixing with water. Such systems also include kits in which the ionomer is employed as a viscous paste, for mixing directly with a second viscous paste that contains as a dispersion the reactive powder.

The term "working time", as used herein, refers to the time between the beginning of the setting reaction, i.e., when the ionomer and reactive powder are combined in the presence of water, and the time the setting reaction has proceeded to the point at which it is no longer practical to perform further physical work upon the system, e.g., spatulate it or reform it, for its intended dental or medical purpose.

The term "setting time", as used herein, refers to the time between the beginning of the setting reaction in a restoration, and the time sufficient hardening has occurred to allow subsequent clinical procedures to be performed on the surface of the restoration. Such hardening can occur either in the course of the normal setting reaction and/or by crosslinking a polymerizable system.

Non-crosslinkable ionomers of the present invention comprise a polymer having sufficient pendent complexing groups to undergo a setting reaction in the presence of a reactive powder and water.

Preferred non-crosslinkable ionomers have the general Formula I:

$$B(X)_m(Z)_p \qquad \text{I}$$

wherein B represents an organic backbone of carbon-carbon bonds, optionally containing non-interfering substituents or linking groups such as oxygen, nitrogen or sulfur heteroatoms, each X independently is a β-dicarbonyl group capable of undergoing a setting reaction in the presence of water and a reactive powder, each Z independently is an ionic group capable of undergoing a setting reaction in the presence of water and a reactive powder, m is a number having an average value of 1 or more, and p is a number having an average value of 0 or more, wherein "m" and "p" represent the average number of pendent X groups and pendent Z groups, respectively, on an average polymer molecule. Preferably m is a number between about 5 and about 500 and p is a number between about 0 and about 1000. More preferably m is a number between about 10 and about 100 and p is a number between about 50 and about 400. Most preferably m is a number between about 20 and about 40 and p is a number between about 100 and about 200.

Preferably the backbone B is an oligomeric or polymeric backbone of carbon-carbon bonds, optionally containing non-interfering substituents or linking groups such as oxygen, nitrogen or sulfur heteroatoms. The term "non-interfering" as used herein refers to substituents or linking groups that do not unduly interfere with its cement reaction with the reactive powder.

Preferred X groups are β-dicarbonyl groups, with β-ketoester groups being particularly preferred. Particularly preferred β-ketoester groups are 2-acetoacetyl groups.

Suitable Z groups are oxy acids of phosphorus in oxidation state III or V, phosphonic acid, halophosphonic acid, oxy acids of sulphur in oxidation state VI or IV, and oxy acids of boron in oxidation state III.

Preferred Z groups are carboxyl, bode and sulphonic groups with carboxyl being particularly preferred.

X and Z groups can be linked to the backbone B directly or by means of any non-interfering organic linking group, such as substituted or unsubstituted alkyl, alkoxyalkyl, aryl, aryloxyalkyl, alkoxyaryl, aralkyl, or alkaryl groups. Preferred non-interfering organic linking groups contain water-solubilizing groups, with 1-vinyl-2-pyrrolidone ("VP") being particularly preferred.

Non-crosslinkable ionomers of Formula I can be prepared according to a variety of synthetic routes, including, but not limited to: (1) reacting a polymer of the formula $B(Z)_{p+i}$, where "p" and "i" are numbers which combined represent the total average number of Z groups on the starting polymer, with a suitable compound in order to form m pendent X groups either through i Z groups thereby leaving p unreacted Z groups, or at other positions, and (2) copolymerizing appropriate monomers, e.g., a monomer containing one or more pendent X groups and a monomer containing one or more pendent Z groups. The second synthetic route referred to above is preferred.

Synthetic route 1, above, can presently be carried out by the use of a "coupling compound", i.e., a compound containing both a pendent group (i.e., an X group) and a reactive group capable of reacting with the polymer through a Z group or through a non-interfering group in order to form a covalent bond between the coupling compound and the Z group or the non-interfering group, thereby linking the pendent group to the backbone B. Suitable coupling compounds are organic compounds, optionally containing non-interfering substituents and/or non-interfering linking groups between the pendent group and the reactive group.

Crosslinkable ionomers of the present invention comprise a polymer having sufficient pendent complexing groups to undergo a setting reaction in the presence of a reactive powder and water, and sufficient pendent polymerizable groups to enable the resulting mixture to be crosslinked by exposure to radiant energy or by a free-radical or cationic mechanism.

Preferred crosslinkable ionomers have the general Formula II:

$$B(X)_m(Y)_n(Z)_p \qquad \text{II}$$

wherein B represents an organic backbone, each X independently is a β-dicarbonyl group capable of undergoing a setting reaction in the presence of water and a reactive powder, each Y independently is a crosslinkable group capable of undergoing a free-radical or cationic crosslinking reaction, each Z independently is an ionic group capable of undergoing a setting reaction in the presence of water and a reactive powder, m is a number having an average value of 1 or more, n is a number having an average value of 1 or more, and p is a number having an average value of 0 or more, wherein "m", "n" and "p" represent the average number of pendent X groups, pendent Y groups and pendent Z groups, respectively, on an average polymer molecule. Preferably m is a number between about 5 and about 500, n is a number between about 1 and about 500 and p is a number between about 0 and about 1000. More preferably m is a number between about 10 and about 100, n is a number between about 10 and about 100 and p is a number between about 50 and about 400. Most preferably m is a number between about 20 and about 40, n is a number between about 20 and about 40 and p is a number between about 100 and about 200.

Preferably the backbone B is an oligomeric or polymeric backbone of carbon-carbon bonds, optionally containing non-interfering substituents or linking groups such as oxygen, nitrogen or sulfur heteroatoms. The term "non-interfering" as used herein refers to substituents or linking groups that do not unduly interfere with either the free-radical or cationic polymerization reaction of the crosslinkable ionomer or its cement reaction with the reactive powder.

Preferred X groups are β-ketoester groups. Particularly preferred ketoester groups are 2-acetoacetyl groups.

Suitable Y groups include, but are not limited to, polymerizable ethylenically unsaturated groups and polymerizable epoxy groups. Ethylenically unsaturated groups are preferred, especially those that can be polymerized by means of a free-radical mechanism, examples of which are substituted and unsubstituted acrylates, methacrylates, alkenes and acrylamides. In aqueous systems, polymerizable groups that are polymerized by a cationic mechanism, e.g., polymerizable ethylenically unsaturated groups such as vinyl ether groups and polymerizable epoxy groups, are less preferred since a free-radical mechanism is typically easier to employ in such systems than a cationic mechanism.

Suitable Z groups are oxy acids of phosphorus in oxidation state III or V, phosphonic acid, halophosphonic acid, oxy acids of sulphur in oxidation state VI or IV, and oxy acids of boron in oxidation state III. Preferred Z groups are carboxyl, boric and sulphonic groups with carboxyl being particularly preferred.

X, Y, and Z groups can be linked to the backbone B directly or by means of any non-interfering organic linking group, such as substituted or unsubstituted alkyl, alkoxyalkyl, aryl, aryloxyalkyl, alkoxyaryl, aralkyl, or alkaryl groups. Preferred non-interfering organic linking groups contain water-solubilizing groups, with 1-vinyl-2-pyrrolidone ("VP") being particularly preferred.

Crosslinkable ionomers of Formula II can be prepared according to a variety of synthetic routes, including, but not limited to: (1) reacting a polymer of the formula $B(Z)_{p+i+j}$, where "p", "i", and "j" are numbers which combined represent the total average number of Z groups on the starting polymer, with a suitable compound in order to form m pendent X groups either through i Z groups, thereby leaving p+j Z groups unreacted with an X group, or at other positions and with a suitable compound in order to form n pendent Y groups either through j Z groups, thereby leaving p+i Z groups unreacted with a Y group, or at other positions; (2) reacting a polymer of the formula $B(X)_m(Z)_{p+j}$, where "m" is a number representing the average number of X groups on the starting polymer and "p" and "j" are numbers which combined represent the total average number of Z groups on the starting polymer, in order to form n pendent Y groups either through j Z groups, thereby leaving p Z groups unreacted with a Y group, or at other positions; and (3) copolymerizing appropriate monomers, e.g., a monomer containing one or more pendent X groups, a monomer containing one or more pendent Y groups and a monomer containing zero or more pendent Z groups.

The first and second synthetic routes referred to above are presently preferred, i.e., the reaction of a polymer with a suitable compound or compounds to form pendent Y groups, as in route (2), or pendent X and Y groups, as in route (1).

Synthetic route 1, above, can presently be carried out by the use of a "coupling compound", i.e., a compound containing both a pendent group (i.e., either an X or a Y group) and a reactive group capable of reacting with the polymer through a Z group or through a non-interfering group in order to form a covalent bond between the coupling compound and the Z group or the non-interfering group, thereby linking the pendent group to the backbone B. Suitable coupling compounds are organic compounds, optionally containing non-interfering substituents and/or non-interfering linking groups between the pendent group and the reactive group.

The second synthetic route referred to above is presently most preferred, i.e., the reaction of suitable compounds with n pendent Y groups to a polymer of the formula $B(X)_m(Z)_{p+j}$ at positions other than the X groups. Such groups can be reacted by the use of a "coupling compound", i.e., a compound containing both a Y group and a reactive group capable of reacting with the polymer through a non-interfering group, thereby linking the Y group to the backbone B in a pendent fashion. Suitable coupling compounds are organic compounds, optionally containing non-interfering substituents and/or non-interfering linking groups between the Y group and the reactive group.

Particularly preferred polymerizable ionomers of Formula II are those in which each X is β-ketoester group and each Y is an ethylenically unsaturated group that can be polymerized by a free-radical mechanism. Such ionomers are conveniently prepared by reacting a polymer backbone (e.g., a polymer of formula $B(X)_m(Z)_{p+j}$ wherein each X is β-ketoester group) with a coupling compound containing both an ethylenically unsaturated group and a group capable of reacting with a carboxylic acid group or a non-interfering group.

Polymers of formula $B(X)_m(Z)_{p+j}$ or $B(Z)_{p+i+j}$ can be prepared by copolymerizing an appropriate mixture of monomers or comonomers. Preferably, such polymers are prepared by free-radical polymerization, e.g., in solution, in an emulsion, or interfacially. Such polymers can be reacted with coupling compounds in the presence of appropriate catalysts, as described more fully in the examples below.

Suitable β-dicarbonyl groups for use in preparing ionomers of the present invention include:

(1) β-diesters having the formula:

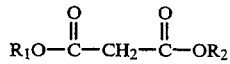

wherein:

$R_1$ and $R_2$ are independently selected from the group consisting of alkyl, preferably containing from 1 to 8 carbon atoms, such as methyl, ethyl, isopropyl, butyl, including substituted alkyl, such as chloromethyl and the like; aryl, preferably containing from 6 to 10 carbon atoms, such as phenyl, including substituted aryl, such as bromophenyl and the like; carbocyclic groups such as cycloaliphatic, such as cyclohexyl and heterocyclic groups, such as pyridyl, and the like; and ethylenically unsaturated groups, such as vinyl, allyl, vinylbenzyl, acrylate, acrylamide, methacrylate, methacrylamide, acryloxyalkyl, methacryloxyalkyl, acrylamidoalkyl, and methacrylamidoalkyl; and wherein at least one of $R_1$ and $R_2$ is a reactive group capable of reacting with the polymer thereby linking the pendent group to the backbone;

(2) β-diketones having the formula:

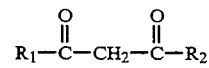

wherein $R_1$ and $R_2$ are as described above, and;

(3) β-ketoesters having the formula:

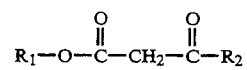

wherein $R_1$ and $R_2$ are as described above.

Coupling compounds suitable for use for preparing the preferred ionomers of the present invention include compounds that contain at least one group capable of reacting with Z, or with a non-interfering group, in order to form a covalent bond, as well as at least one polymerizable ethylenically unsaturated group or a β-dicarbonyl group. When Z is carboxyl, a number of groups are capable of reacting with Z, including both electrophilic and nucleophilic groups. Examples of such groups include the following moieties, and groups containing these moieties: -OH, -NH₂, -NCO, -COCl, and

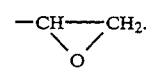

When the attaching site is an alcohol, a number of groups are capable of reacting with the alcohol. Examples of such groups include the following moieties, and groups containing these moieties: -NCO, -COCl ,

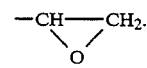

Examples of suitable coupling compounds to attach Y groups include, for example, acryloyl chloride, methacryloyl chloride, vinyl azalactone, allyl isocyanate, 2-hydroxyethylmethacrylate, 2-aminoethylmethacrylate, and 2-isocyanatoethylmethacrylate. Other examples of suitable coupling compounds include those described in U.S. Pat. No. 4,035,321, the disclosure of which is hereby incorporated by reference. Examples of preferred coupling compounds include, for example, the following methacrylate compounds and their corresponding acrylates:

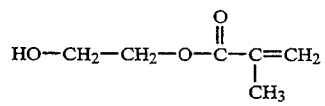

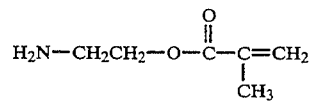

-continued

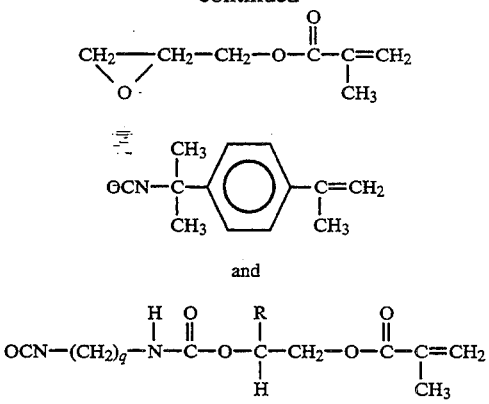

and

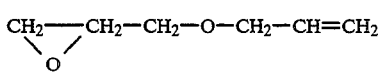

the following allyl compound:

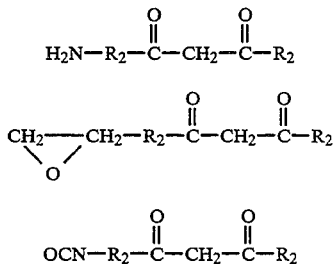

as well as the following β-dicarbonyl compounds:

$$H_2N-R_2-\overset{O}{\overset{\|}{C}}-CH_2-\overset{O}{\overset{\|}{C}}-R_2$$

$$\underset{O}{\overset{CH_2-CH_2}{\diagdown\diagup}}-R_2-\overset{O}{\overset{\|}{C}}-CH_2-\overset{O}{\overset{\|}{C}}-R_2$$

$$OCN-R_2-\overset{O}{\overset{\|}{C}}-CH_2-\overset{O}{\overset{\|}{C}}-R_2$$

wherein q is 1 to 20, R is H or lower alkyl (e.g., having 1 to 6 carbon atoms), and $R_2$ is alkyl or alkoxyalkyl and preferably contains from 1 to 8 carbon atoms.

Particularly preferred coupling compounds are the following methacrylate compounds and their corresponding acrylates, wherein R and q are as defined above.

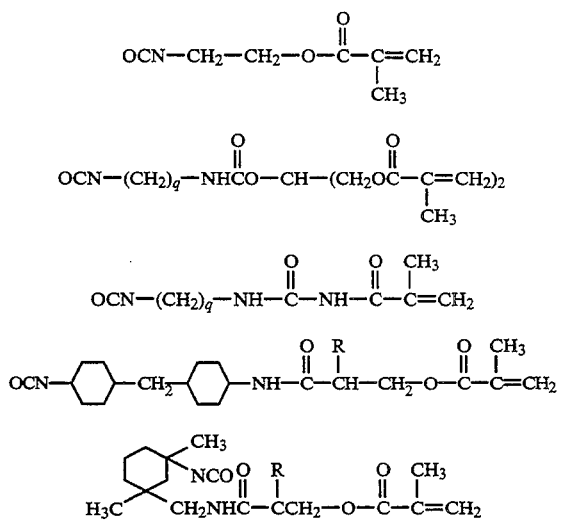

Preferred crosslinkable ionomers of Formula II are prepared by reacting a polymer of formula $B(X)_m(Z)_{p+j}$ wherein X is a β-ketoester group with a coupling compound containing a reactive group of the formula NCO. The resultant ionomers, e.g., those of Formula II above wherein the covalent bond between the Z group or a non-interfering group and the reactive group of the coupling compound is an amide linkage or a urethane linkage, provide an optimal combination of such properties as adhesion to dentin, mechanical strength, working time, fluoride release and the like.

The molecular weight of the resultant ionomers of either Formula I or II is preferably between about 1000 and about 500,000, more preferably between about 5,000 and about 100,000, and most preferably between about 10,000 and about 40,000. These ionomers are generally water-miscible, but to a lesser extent than the polymer backbone from which they are derived. Hence, the use of cosolvents, as described more fully below, is preferred in order to enhance the solubility of the ionomers and achieve more concentrated solutions thereof.

Ionomer cements of the present invention may optionally contain conventional polyalkenoic acid polymers in addition to the ionomer polymers mentioned above. Suitable polyalkenoic acids for use in preparing ionomer cements of this invention include those homopolymers and copolymers of unsaturated mono-, di-, or tricarboxylic acids commonly used to prepare glass ionomer cements. Representative polyalkenoic acids are described, for example, in U.S. Pat. Nos. 3,655,605, 4,016,124, 4,089,830, 4,143,018, 4,342,677, 4,360,605 and 4,376,835.

Presently preferred polyalkenoic acids are polymers prepared by the homopolymerization and copolymerization of unsaturated aliphatic carboxylic acid monomers, for example acrylic acid, 2-chloroacrylic acid, 3-chloroacrylic acid, 2-bromoacrylic acid, 3-bromoacrylic acid, methacrylic acid, iraconic acid, maleic acid, glutaconic acid, aconitic acid, citraconic acid, mesaconic acid, fumaric acid and tiglic acid.

Suitable monomers that can be copolymerized with the unsaturated aliphatic carboxylic acids include unsaturated aliphatic compounds such as acrylamide, acrylonitrile, vinyl chloride, allyl chloride, vinyl acetate, and 2-hydroxyethyl methacrylate. Ter- and higher polymers may be used if desired. The polyalkenoic acid should be surgically acceptable, that is, it should be substantially free from unpolymefized monomers and other undesirable components.

Particularly preferred polyalkenoic acids also include homopolymers of polyacrylic acid, and copolymers of acrylic and itaconic acids, acrylic and maleic acids, methyl vinyl ether and maleic arthydride or maleic acid, ethylene and maleic anhydride or maleic acid, and styrene and maleic anhydride or maleic acid.

The preferred crosslinkable ionomers of the present invention can be formulated in water, either alone or with the use of adjuvants such as cosolvents described in greater detail below. The preferred concentration of ionomer in aqueous solution is between about 10 and about 70 percent by weight, based on the weight of the final aqueous solution, and more preferably is between about 20 and about 50 percent by weight. For optimal use in preparing a cement of the present invention, the preferred viscosity of the ionomer solution is between about 60 and about 2000 centistokes, and most preferably between about 300 and about 1500 centistokes. Ionomer solutions having higher viscosities will generally be more difficult to mix, and solutions of lower molecular weight ionomer will generally provide cements having lower strength.

In order to prepare a crosslinkable ionomer cement from the cement system of this invention, a crosslinkable ionomer is mixed with a reactive powder in the presence of water. Alternatively, the crosslinkable ionomer is mixed with a reactive powder in the presence of water and an acid. Acids for use in the present invention can be inorganic or organic acids, arid if organic can be monomeric, oligomeric or polymeric. If desired, a precursor to the acid such as acid arthydride, acid halide (including inorganic acid halides such as Lewis acids and organic acid halides), or ester can be used in place of the acid itself, e.g., to generate the desired acid in situ. Suitable acids include mineral acids, carboxylic acids, sulfonic acids, and phenols, with carboxylic acids, alkylsulfonic acids, and arylsulfonic acids being preferred. Optionally, and preferably, the cement system also includes a polymerization initiator, thereby providing the ability to achieve a shorter cure time when preparing the resultant cement.

Reactive powders suitable for use in the cement systems of this invention include those that are commonly used with ionomers to form ionomer cements.

Suitable reactive powders include glasses such as:
(I) $SiO_2$-$Al_2O_3$-$CaO$ and
(II) $SiO_2$-$Al_2O_3$-$CaF_2$.

More complex glasses, e.g., four or more component glasses, may also be utilized. Examples of suitable reactive powders are described in the Prosser et al. article cited above, the disclosure of which is hereby incorporated by reference, as well as metal oxides such as zinc oxide and magnesium oxide, and ion-leachable glasses, e.g., as described in U.S. Pat. Nos. 3,655,605, 3,814,717, 4,143,018, 4,209,434, 4,360,605 and 4,376,835.

Particularly preferred reactive powders for use in the cement systems of this invention are those that contain leachable fluoride, since the sustained release of fluoride ions as a byproduct of the setting reactions provides carlostatic benefits. Examples of preferred powders include fluoroaluminosilicate and fluoroaluminoborate ion-leachable glasses.

The crosslinkable ionomer cement systems of the invention can frequently be polymerized without the use of one or more polymerization initiators, e.g., by the use of thermal energy or by exposure to a high energy pulsed xenon source. Optionally, and preferably, the ionomer cement system contains one or more suitable polymerization initiators that act as a source of free-radicals when activated. Such initiators can be used alone or in combination with one or more accelerators and/or sensitizers.

Polymerization initiators suitable for use in the present invention include electromagnetic radiation-induced polymerization initiators, such as ultraviolet- or visible-light-induced polymerization initiators, that exhibit a desired combination of such properties as stability and efficiency of free-radical production and polymerization initiation.

Examples of suitable ultraviolet-induced polymerization initiators include, but are not limited to, ketones such as benzil and benzoin, and acyloins and acyloin ethers, commercially available, for example, from Aldrich Chemical Co. Preferred ultraviolet-induced polymerization initiators include 2,2-dimethoxy-2-phenylacetophenone ("Irgacure 651") and benzoin methyl ether (2-methoxy-2-phenylacetophenone), both commercially available from Ciba-Geigy Examples of suitable visible-light-induced initiators include, but are not limited to, diaryliodonium salts and triarylsulfonium salts, as well as chromophore substituted halomethyl-s-triazines, such as those described in U.S. Pat. No. 3,954,475, and halomethyl oxadiazoles such as those described in U.S. Pat. No. 4,212,970. Such initiators can be used alone or in combination with suitable accelerators, e.g., amines, peroxides, and phosphorus compounds, and/or with suitable photosensitizers, e.g., ketone or alpha-diketone compounds such as, e.g., camphorquinone.

For crosslinkable ionomers that are polymerized by a cationic mechanism, suitable initiators include salts that are capable of generating cations such as the diaryliodonium, triarylsulfonium and aryldiazonium salts.

Preferred visible light-induced polymerization initiator systems include suitable combinations of a diketone, e.g., camphorquinone, and a diaryliodonium salt, e.g., diphenyliodonium chloride, bromide, iodide or hexafluorophosphate, with or without additional hydrogen donors, or accelerators, such as sodium benzene sulfinate, amines or amine alcohols.

Polymerization initiator, when employed, is preferably present in the ionomer cement system in an amount sufficient to achieve the desired extent of polymerization. Such amount is dependent in part on the extinction coefficient of the initiator and the thickness of the layer to be exposed to radiant energy. Typically, an ultraviolet-induced polymerization initiator will be present at about 0.01% to about 5%, based on the weight of the ionomer(s) present, and the components of a visible light-induced polymerization initiator system will generally be present at a combined weight of about 0.01 to 5%, and preferably from about 0.1 to 5%, based on the weight of the ionomer(s) present.

Polymerization initiators suitable for use in the present invention include redox initiators that exhibit a desired combination of such properties as stability and efficiency of free-radical production and polymerization initiation and water miscibility.

The water-soluble reducing agent and water-soluble oxidizing agent are most conveniently discussed together. They should react with or otherwise cooperate with one another to produce free-radicals capable of crosslinking the ethylenically-unsaturated moiety. The reducing agent and oxidizing agent preferably are sufficiently shelf-stable and free of undesirable colorization to permit their storage and use under typical dental conditions. They should be sufficiently water-soluble to permit ready dissolution in (and discourage separation from) the other components of the cement. The reducing agent and oxidizing agent should also be sufficiently soluble and present in an amount sufficient to permit an adequate free-radical reaction rate. This can be evaluated by combining all of the ingredients of the cement except for the filler under safelight conditions, and observing whether or not a hardened mass is obtained.

Preferred reducing agents include ascorbic acid, cobalt (II) chloride, ferrous chloride, ferrous sulfate, hydrazinc, hydroxylamine (depending upon the choice of oxidizing agent), oxalic acid, thiourea, and salts of a dithionite or sulfite anion. Preferred oxidizing agents include potassium persulfate, cobalt (III) chloride, tert-butyl hydroperoxide, ferric chloride, hydroxylamine (depending upon the choice of reducing agent), perboric acid and its salts, and salts of a permanganate or persulfate anion with potassium persulfate presently preferred. Hydrogen peroxide can also be used, although it has been found to interfere with the photoinitiator in some instances.

The amount of reducing agent and oxidizing agent should be sufficient to provide the desired degree of crosslinking of the ethylenically-unsaturated component. The preferred amount for each of the reducing agent and oxidizing agent is about 0.01 to about 10%, more preferably about 0.02 to about 5%, based on the total weight (including water) of the unset cement components.

The components of the ionomer cement system can be combined, e.g., blended or mixed, in a variety of manners and amounts in order to form the crosslinkable ionomer cement of this invention. Suitable combining techniques include those commonly employed to mix ionomer cement systems. In one suitable technique, a concentrated aqueous solution of ionomer is mixed with reactive powder at the time of use. The resultant combination of ionomer, powder and water allows the setting reaction to begin. In an alternative technique, the ionomer and powder are provided as a powdered blend under substantially anhydrous conditions, i.e., conditions in which there is not sufficient water to allow the setting reaction to proceed. Such systems can then be combined with water at the time of use in order to begin the setting reaction. In a second alternative technique, the ionomer is employed as a viscous paste, for mixing directly with a second viscous paste that contains as a dispersion the reactive powder.

The ratio of powder (i.e., reactive powder or powdered blend of ionomer and reactive powder) to liquid in such techniques is an important factor in determining the workability of the mixed ionomer cement systems. Ratios higher than about twenty to one (powder to liquid, by weight) tend to exhibit poor workability, while ratios below about one to one (powder to liquid, by weight) tend to exhibit poor mechanical properties, e.g., strength, and hence are not preferred. Preferred ratios of powder to liquid by weight are on the order of about one to one to about five to one.

If desired, the cements of the invention can contain adjuvants such as pigments, nonvitreous fillers, inhibiters, accelerators, viscosity modifiers, surfactants, and other ingredients that will be apparent to those skilled in the art. Optional other ingredients, such as polymerization initiators, modifying agents and cosolvents can be added at any time and in any manner that does not prematurely begin the setting reaction or the crosslinking reaction. Modifying agents and chelating agents can be used in the ionomer cement systems of the present invention in order to provide prolonged working times. Examples of suitable modifying agents are described in applicant's copending U.S. patent application Ser. No. 07/605,749, the disclosure of which is hereby incorporated by reference. Examples of suitable chelating agents, such as tartaric acid, are described in U.S. Pat. Nos. 4,089,830, 4,209,434, 4,317,681, 4,374,936, and 4,758,612.

Cosolvents useful in the present invention include, but are not limited to, low molecular weight organic solvents. The word "cosolvent", as used herein refers to a material that aids in the dissolution of an ionomer in water, in order to form a homogeneous aqueous solution of cosolvent and ionomer. Suitable cosolvents include non-copolymerizable organic solvents and copolymerizable low molecular weight hydrophilic alkenyl solvents. The word "copolymerizable" as used herein refers to the ability of the cosolvent to cure compatibly with the ionomers used in the invention. Copolymerizable cosolvents can be added to the ionomer cement systems of this invention for a variety of reasons, for instance, to provide a homogeneous solution of a crosslinkable ionomer having inherently low aqueous solubility, to shorten the exposure of radiant energy needed to cure the system, or to vary the physical properties, e.g., the flexibility, of the resultant cured ionomer cement. Examples of suitable cosolvents include non-copolymerizable cosolvents such as ethanol, propanol, and glycerol, and copolymerizable cosolvents such as 2-hydroxylethylmethacrylate or 2-hydroxypropylmethacrylate.

Sufficient amounts of each component in the cement systems of the present invention should be employed to obtain the desired working time. Preferably such systems will provide a working time of at least about one minute and less than about 30 minutes and most preferably greater than two minutes and less than about 20 minutes, during which time the systems can be cured by exposure to an appropriate source of radiant energy or by a free-radical or cationic mechanism. For the sake of brevity this discussion will focus on dental applications, and particularly, the curing of such systems in situ, e.g., in the mouth of a patient.

One method of curing the ionomer cement system is accomplished by exposure to any source of radiant energy capable of causing the desired extent of polymerization of the crosslinkable ionomer. Suitable radiant energy sources afford a desired combination of such properties as safety, controllability, suitable intensity, and suitable distribution of incident energy. For a general discussion, see "Radiation Curing", Kirk-Othmer Encyclopedia of Chemical Technology, 3d Ed., Vol. 19, pp. 607–624 (1982). Preferred radiant energy sources are ultraviolet or visible light sources whose emission spectra correspond closely with the absorption range of the polymerization initiator in the ionomer cement system. For instance, sources emitting ultraviolet light at wavelengths between about 335 and 385 nm, and sources emitting visible light in the blue region at wavelengths between about 420 and 480 nm are preferred for use with the preferred ultraviolet and visible-light-induced polymerization initiators, respectively. For polymerizing cement systems in the mouth, visible light radiation such as that provided by standard dental curing lights is particularly preferred.

Upon exposure of an ionomer cement system of the present invention to an appropriate source of radiant energy, the system rapidly begins to cure, e.g., within about 45 seconds, and preferably within about 30 seconds. The restoration generally exhibits the greatest degree of cure at its surface, where the radiant energy is most intense. The surface of the restoration therefore can be crosslinked sufficiently to allow subsequent procedures to be performed on the restoration, while the interior of the restoration is allowed to harden fully by means of the ongoing setting reaction or by an ongoing redox reaction. Thus, if the radiant energy exposure step is omitted, the usual setting and redox crosslinking will occur, ultimately resulting in the hardening of the material, even in the dark. This phenomenon offers a unique advantage in that a relatively deep restoration can be prepared by rapidly crosslinking the outer surface of the restoration instantly by exposure to radiant energy, allowing the inner portions of the restoration to cure more slowly by the usual setting reaction and/or the ongoing redox reaction. As a result, the dentist can continue to carry out further restorative procedures, e.g., layering further ionomer cement on the hardened surface, while the inner portions continue to harden. This can result in a substantial saving of time for the practitioner and patient.

The ionomer cements of this invention can be used in a variety of applications in the dental or medical fields in which a bulk curable material of low shrinkage, increased resistance to degradation by water, and that will adhere well to the surrounding tooth or bone structure is desired. For instance, these cements can be used as dental restoratives for lining or basing Class I, II, III and V restorations, for cementation, as sealants, and as bulk filling materials.

The present invention will be further understood in view of the following examples which are merely illustrative and not meant to limit the scope of the invention. Unless otherwise indicated, all parts and percentages are by weight.

EXAMPLE 1

Synthesis of Non-crosslinkable Ionomer Containing β-Ketoester and Pendent Carboxyl Groups A non-crosslinkable ionomer was prepared from the ingredients set out below in TABLE I:

TABLE I

| Ingedient (in parts) | Example No. 1 |
| --- | --- |
| Acrylic acid | 5.76 |
| Itaconic acid | 2.60 |
| AAEM[1] | 4.28 |
| AIBN[2] | 0.09 |
| THF[3] | 66.40 |

[1]"AAEM" = 2-Acetoacetoxyethyl methacrylate.
[2]"AIBN" = Azobisisobutyronitrile.
[3]"THF" = Tetrahydrofuran.

The itaconic acid was dissolved in THF in a glass reactor. Acrylic acid, AAEM and AIBN were then added sequentially to give a clear solution. The reaction vessel was fitted with nitrogen inlet tube, thermometer and reflux condenser. The reaction mixture was flushed with nitrogen for 15 minutes and then heated for 4 hours at 65°–70° C. A further portion of AIBN (0.09 parts) was then added to stop the reaction and the heat was turned off. A portion of the THF was evaporated which caused part of the polymer to separate out. The reaction mixture was precipitated in 10 volumes of ethyl acetate, filtered, washed and then dried in vacuo.

EXAMPLES 2–3

Synthesis of Crosslinkable Ionomers Containing β-Ketoester and Pendent Hydroxy Groups Two crosslinkable ionomers were prepared from the ingredients set out below in TABLE II:

TABLE II

| Ingredient (in parts) | Example No. 2 | Example No. 3 |
| --- | --- | --- |
| STEP I | | |
| AAEM | 1.6 | 1.6 |
| GM[1] | 2.14 | 2.14 |
| THF | 17.8 | 4.45 |
| AIBN | 0.013 | 0.013 |
| STEP II | | |
| DBTDL[2] | 0.206 | 0.067 |
| BHT[3] | 0.01 | 0.01 |
| THF | 17.8 | 6.67 |
| IEM[4] | 0.31 | 0.62 |
| THF | 4.44 | 2.22 |

[1]"GM" = 2-Glyceryl methacrylate.
[2]"DBTDL" = Dibutyltin dilaurte.
[3]"BHT" = Butylated hydroxytoluene.
[4]"IEM" = 2-Isocyanatoethyl methacrylate.

For STEP I of each Example, the AIBN was added to a solution of AAEM and GM in THF. Each reaction mixture was flushed with nitrogen for 15–20 minutes and then heated at 60° C. under nitrogen atmosphere for 18 hours. In STEP II, to each resultant viscous mixture were added DBTDL and BHT in THF, followed by the addition of IEM dissolved in THF. An air bleed was introduced and each mixture heated at 45° C. for 14 hours. Each reaction mixture was precipitated in ethyl acetate and dried in vacuo. Infrared spectral analysis confirmed the presence of ethylchic unsaturation, β-ketoester groups and pendent hydroxy groups.

EXAMPLE 4

Synthesis of Crosslinkable Ionomer Containing β-Ketoester and Pendent Carboxyl Groups A crosslinkable ionomer was prepared from the ingredients set out below in TABLE III:

TABLE III

| Ingredient (in parts) | Example No. 4 |
| --- | --- |
| Acrylic acid | 5.76 |
| Itaconic acid | 2.60 |
| AAEM | 4.28 |
| AIBN | 0.09 |
| THF | 66.4 |
| IEM | 3.1 |

The itaconic acid was dissolved in THF in a glass reactor. Acrylic acid, AAEM and AIBN were then added sequentially to give a clear solution. The reaction vessel was fitted with nitrogen inlet tube, thermometer and reflux condenser. The reaction mixture was flushed with nitrogen for 15 minutes and then heated for 4 hours at 65°–70° C. The reaction mixture was cooled to 35°–40° C. and the nitrogen inlet was replaced with an air inlet tube. BHT (0.05 parts) and DBTDL (1.05 parts) were added, followed by the dropwise addition of IEM dissolved in 4.2 parts of THF. The reaction was allowed to proceed for a further period of 1 hour. The polymer was precipitated in ten volumes of ethyl acetate, filtered, washed with more ethyl acetate and then dried.

EXAMPLES 5–7

Synthesis of Crosslinkable Ionomers Containing β-Ketoester And Pendent Pyrrolidone Groups Three crosslinkable ionomers were prepared from the ingredients set out below in TABLE IV:

TABLE IV

| Ingredient (in parts) | Example No. 5 | Example No. 6 | Example No. 7 |
| --- | --- | --- | --- |
| AAEM | 8.56 | 12.8 | 6.42 |
| VP[1] | 4.44 | 2.2 | 3.33 |
| Acrylic Acid | 1.45 | 1.44 | 2.88 |
| IEM | 3.1 | 3.1 | 6.2 |

[1]"VP" = 1-vinyl-2-pyrrolidone.

For each Example, the first three ingredients listed in TABLE IV and 0.16 parts AIBN were dissolved in 66.38 parts THF and charged into a three-necked glass reaction vessel fitted with mechanical stirrer, nitrogen inlet tube, addition funnel and thermometer. Each reaction mixture was flushed with nitrogen for 15 minutes and then heated at 60° C. under nitrogen atmosphere or 20 hours. To each resultant viscous mixture were added 0.266 parts DBTDL and 0.01 parts BHT in 22.15 parts THF. Each reaction mixture was cooled to 40° C. and an air bleed introduced. This was followed by the slow addition of the amount of IEM listed in TABLE IV. Each reaction mixture was allowed to stir at 40° C. for an additional 3.5 hours. Each mixture was added to a 10-fold excess of ethyl acetate, followed by filtration, washing, and drying in vacuo. The structure of each reaction product was confirmed by nuclear magnetic resonance spectral analysis. The weight average molecular weight ("$M_w$") of the reaction product of Ex. No. 5 and Ex. No. 7 was determined by get permeation chromatography ("GPC") to be 65,300 and 55,300 respectively with a polydispersity of 3.54 and 2.54 respectively.

EXAMPLES 8–13

Preparation of Ionomer Liquids

Ionomer liquids were formulated by mixing together the ingredients set out below in TABLE V:

TABLE V

| Ingredient (in parts) | Example No. | | | | | |
|---|---|---|---|---|---|---|
| | 8 | 9 | 10 | 11 | 12 | 13 |
| Ionomer[1] | 0.60 | 0.51 | 4.0 | 5.2 | 4.5 | 4.5 |
| HEMA[2] | 0.94 | 0.45 | — | 4.76 | — | — |
| TAMG[3] | — | — | — | — | 3.5 | — |
| Water[4] | 1.40 | 0.73 | 2.4 | 7.14 | 1.0 | 5.5 |
| Copoly 4:1 (Acrylic:Itaconic) Acid[5] | 0.61 | 0.51 | — | 5.2 | 3.0 | — |
| CPQ[6] | 0.01 | 0.0025 | 0.05 | 0.05 | 0.03 | — |
| $(C_6H_5)_2I^+PF_6^-$ | — | — | — | — | 0.012 | — |
| BHT | — | — | — | — | 0.006 | — |
| GMA[7] | — | — | 3.6 | — | — | — |

[1]Examples 8–10 were prepared using the ionomers of Examples 2–4 respectively. Examples 11 and 12 were prepared using the ionomer of Example 6. Example 13 was prepared using the ionomer of Example 1.
[2]"HEMA" = 2-Hydroxyethyl methacrylate.
[3]"TAMG" = Tetracrylamidomethyl glycouril.
[4]Distilled water.
[5]Ethylenically unsaturated acidic copolymer prepared like the precipitated dry polymer of EXAMPLE 11 of European Published Pat. Application No. 0 323 120.
[6]"CPQ" = Camphoroquinone.
[7]"GMA" = Glyceryl dimethacrylate.

For each Example, the ingredients were stirred at room temperature (25° C.) under safelight conditions until a homogeneous solution was obtained. The crosslinkable solutions (Ex. No. 8–12) were protected from exposure to ambient or artificial light by storage in an opaque container.

EXAMPLE 14

Preparation of Ionomer Liquid with Additional Protonic Acid

To 3 parts AAEM/VP polymer of Example 6 was added 17 parts water and 1 part ethanol. Hydrochloric acid ("HCl") was added to the solution to bring the pH to 1.5.

EXAMPLES 15–21

Preparation of Surgical Cements

The ingredients set out below in TABLE VI were mixed, melted in an arc furnace at about 1350°–1450° C., poured from the furnace in a thin stream and quenched using chilled rollers to provide an amorphous single-phase fluoroaluminosilicate glass:

TABLE VI

| Ingredient | Parts by Weight |
|---|---|
| $SiO_2$ | 27.00 |
| $Al_2O_3$ | 0.80 |
| $P_2O_5$ | 0.94 |
| $AlF_3$ | 23.00 |
| $Na_2AlF_6$ | 10.65 |
| $ZnO$ | 21.00 |
| $MgO$ | 2.12 |
| $SrO$ | 12.55 |
| $B_2O_3$ | 1.94 |

98 Parts of the glass were ball-milled with 2 parts diphenyliodonium hexafluorophosphate to provide a pulverized frit which was screened through a 44 micron mesh screen. Surface area was measured using the Brunauer, Emmet and Teller (BET) method and determined to be 1.1–1.3 $m^2/g$.

The ionomer liquids of Examples 8–14 were independently mixed with the above prepared glass at a powder:liquid ratio of 1.4:1.0 to provide the cements of Examples 15–21 respectively. Each mixture was hand spatulated at about 20° C. for approximately 10 seconds to provide a smooth creamy cement. A sample of each of the cement mixtures of Examples 15, 16 and 18 was placed on a mixing pad and irradiated with a "VISI-LUX 2" dental curing light (3M) for 20 seconds. A hard, cured cement was obtained that showed no indentation when impressed with a 400 g Gilmore needle per ISO specification 7489. Samples of the cement of Example 15 were used to measure adhesion to dentin and other samples of each cement were used to measure diametral tensile strength ("DTS") and compressive strength ("CS") of the cured cement.

For measurement of adhesion to dentin, bovine teeth of similar age and appearance were partially embedded in circular acrylic disks so that the enamel was exposed. The exposed portion of each tooth was ground flat and parallel to the acrylic disk using Grade 120 silicon carbide paper-backed abrasive mounted on a lapidary wheel, until the dentin was exposed. Further grinding and polishing of the teeth was carried out by mounting Grade 320 and then Grade 600 silicon carbide paper-backed abrasive on the lapidary wheel. During the grinding and polishing steps, the teeth were continuously rinsed with water. The polished teeth were stored in distilled water and used for testing within 2 hours after polishing. The polished teeth were removed from the water and dried using a stream of compressed air.

A 0.250 mm thick and 19.05 mm square tape film with a 5 mm diameter circular hole through the film was placed over the exposed dentin of the polished tooth. A 1.4:1.0 powder:liquid cement mixture that had been hand-spatulated at about 20° C. for about 30 seconds was placed in the hole and cured with a VISILUX 2 curing light for 30 seconds. The tape was removed without disturbing the cement layer and a thin layer of "SCOTCHBOND 2" dental adhesive (available from 3M Company, St. Paul, Minn. 55144) was applied to the cement layer. The adhesive was cured with a VISI-LUX ™ 2 curing light for 20 seconds. A mold made from a 2.5 mm thick polytetrafluoroethylene sheet with a 5 mm diameter circular hole through the sheet was fitted with a sleeve made from a no. 4 gelatin capsule and clamped to each polished tooth coaxially with the cured cement. The gelatin capsule sleeve was then filled with "P-50" light cure resin bonded ceramic restorative (3M, universal shade) and cured with a VISILUX ™ 2 curing light for 30 seconds, allowed to stand for about 5 minutes at room temperature, then stored in distilled water at 37° C. for 24 hours. The molds were then carefully removed, leaving a molded cement button attached to each tooth.

Adhesive strength was evaluated by mounting the acrylic disk in a holder clamped in the jaws of an "IN-STRON" tensile testing apparatus with the polished tooth surface oriented parallel to the direction of pull. A loop of 0.44 mm diameter orthodontic wire was placed around the base of the cement button adjacent to the polished tooth surface. The ends of the orthodontic wire were clamped in the pulling jaw of the tensile testing apparatus, placing the bond in shear stress. The bond was stressed until it (or the cement button) failed, using a crosshead speed of 2 mm/min. The average adhesion value for six specimens for the cement of Example 15 was 6.53 Mpa.

For DTS and CS measurements, the ionomer liquids of Examples 8-14 were independently hand spatulated with the glass for one minute at a 1.4:1.0 powder:liquid ratio, then packed into, a 4 mm inside diameter glass tube, capped with silicone rubber plugs, and axially compressed at about 0.28 Mpa. About 1.5 minutes after the start of mixing, the samples of Examples 15-19 were exposed for 80 seconds to light from two oppositely-disposed VISILUX 2 curing lamps and then the axial pressure was removed. The samples were allowed to stand for one hour at ambient pressure, 90%+ relative humidity and 37° C. The samples were cut on a diamond saw to form cylindrical plugs 2 mm long for measurement of DTS and 8 mm long for measurement of CS. The plugs were stored in distilled water at approximately 37° C. for about 24 hours. DTS and CS values were determined according to ISO specification 7489, using a crosshead speed of 1 mm/rain and an average of at least 5 samples.

The DTS and CS of the cements of Examples 15-21 were measured and the values are set out below in TABLE VII. As a control, VITREBOND powder and liquid were mixed at a 1.4:1.0 powder:liquid ratio and the DTS and CS measured as described above for Examples 15-19. As a comparison, the DTS and CS, as cited in the literature, of another commercially available cement, "KETACBOND" (available for ESPE Premier Sales Co., Norristown, Pa. 19404) are provided in TABLE VII.

TABLE VII

| Ex. No. | Ionomer Liquid of Ex. No. | DTS (MPa.) | CS (MPa.) |
|---|---|---|---|
| 15 | 8 | 14.3 | 82.1 |
| 16 | 9 | 10.5 | 51.4 |
| 17 | 10 | 19.4 | 142.8 |
| 18 | 11 | 12.4 | 84.8 |
| 19 | 12 | 19.3 | 136.6 |
| 20 | 13 | 16.6 | 102.1 |
| 21 | 14 | 9.1 | 22.9 |
| VITREBOND | | 13.9 | 90.3 |
| KETACBOND | | 5.5 | 69.0 |

EXAMPLE 22

Solubility of Surgical Cements

Two sample disks of the cement of Example 19 were prepared according to the procedure of ISO 7489. Freshly mixed cement was placed in a mold and a nichrome wire was embedded into each disk. The specimens were exposed to a VISILUX 2 curing light for 60 seconds, followed by storage for 1 hour at 37° C. and 90%+ relative humidity.

Two commercially available cements, VITREBOND and KETACBOND were similarly prepared. The KETACBOND samples were not light cured, but were put in a 37° C. oven for 1 hour instead.

The prepared samples of each cement were suspended in 50 ml of water in a taxed bottle. The bottles were placed in a 37° C. oven for 23 hours. The samples were then removed and the water allowed to evaporate. The solubility of each cement was determined according to ISO 7489 and is set out below in TABLE VIII.

TABLE VIII

| Cement | Solubility in Water % |
|---|---|
| Ex. No. 19 | 0.06 |
| VITREBOND | 0.17 |
| KETACBOND | 0.30 |

The data of TABLE VIII show that a substantial decrease in water solubility was observed for a cement of the present invention compared to the water solubility of two commercially available cements.

COMPARATIVE EXAMPLES 1-3

A polycarboxylic acid ionomer was prepared from the ingredients set out below in TABLE IX:

TABLE IX

| Ingredient | Parts |
|---|---|
| Acrylic acid | 5.7 parts |
| Itaconic acid | 2.6 parts |
| AIBN | 0.08 parts |
| THF | 66 parts |

The itaconic acid was dissolved in THF in a glass reactor. Acrylic acid and AIBN were then added sequentially to give a clear solution. The reaction vessel was fitted with nitrogen inlet tube, thermometer and reflux condenser. The reaction mixture was flushed with nitrogen for 15 minutes and then heated for 4 hours at 65°-70° C. The reaction mixture was allowed to cool down and then precipitated in ten volumes of ethyl acetate, filtered, washed and then dried in vacuo.

Three ionomer liquids were formulated by mixing together the ingredients set out below in TABLE X.

TABLE X

| Ingredient (in parts) | Example No. | | |
|---|---|---|---|
| | C1 | C2[1] | C3 |
| Ionomer of this example | 2.25 | 2.25 | 2.25 |
| Water | 2.75 | 2.75 | 2.75 |
| Aluminum acetylacetonate | — | 0.50 | — |
| Ethyl acetoacetate | — | — | 0.50 |

[1]This mixture was shaken for four hours at room temperature but the solid failed to dissolve into the liquid phase.

Surgical cements were prepared and tested as described for Examples 20 and 21. The DTS and CS of the cements of Comparative Examples C1 and C3 were measured and the values set out in TABLE XI. Examples 20 and 17 are also listed for comparison.

TABLE XI

| Ex. No. | DTS (MPa.) | CS (MPa.) |
|---|---|---|
| C1 | 13.0 | 68.3 |
| C3 | 11.3 | 60.7 |
| 20 | 16.6 | 102.1 |
| 17 | 19.4 | 142.8 |

I claim:

1. A polymer of the formula:

$$B(X)_m(Y)_n(Z)_p$$

wherein B represents an organic backbone;
  each X independently is a β-dicarbonyl group capable of undergoing a setting reaction in the presence of water.
  each Y independently is a crosslinkable group capable of undergoing a free-radical or cationic crosslinking reaction,
  each Z independently is an ionic group capable of undergoing a setting reaction in the presence of water,
  m is a number having an average value of 1 or more,
  n is a number having an average value of 1 or more,
  p is a number having an average value of 0 or more,
  and wherein said polymer has a weight average molecular weight between 1,000 and 500,000.

2. A polymer according to claim 1, wherein m is a number having an average value between about 5 and about 500.

3. A polymer according to claim 1, wherein m is a number having an average value between about 10 and about 100.

4. A polymer according to claim 1, wherein m is a number having an average value between about 20 and about 40.

5. A polymer according to claim 1, wherein n is a number having an average value between about 1 and about 500.

6. A polymer according to claim 1, wherein n is a number having an average value between about 10 and about 100.

7. A polymer according to claim 1, wherein n is a number having an average value between about 20 and about 40.

8. A polymer according to claim 1, wherein p is a number having an average value between about 0 and about 1000.

9. A polymer according to claim 1, wherein p is a number having an average value between about 50 and about 400.

10. A polymer according to claim 1, wherein p is a number having an average value between about 100 and about 200.

11. A polymer according to claim 1, wherein m is a number having an average value between about 20 and about 40, n is a number having an average value between about 20 and about 40, and p is a number having an average value between about 100 and about 200.

12. A polymer according to claim 1, wherein said one or more β-dicarbonyl groups are selected from the group consisting of β-ketoester groups, β-diester groups, and β-diketone groups.

13. A polymer according to claim 1, wherein said one or more β-dicarbonyl groups are β-ketoester groups.

14. A polymer according to claim 1, wherein said ionic group is an alkenoic acid group.

15. A polymer according to claim 1, wherein said ionic group is selected from the group consisting of carboxyl groups, boric groups, phosphonic groups, and sulphonic groups.

16. A polymer according to claim 13, wherein said alkenoic acid group is a carboxyl group.

17. A polymer according to claim 1, wherein said crosslinking group is selected from the group consisting of epoxies, acrylates, methacrylates, alkenes, acrylamides, and vinyl ethers.

18. A polymer according to claim 11, wherein said polymer has a weight average molecular weight between 5,000 and 100,000.

19. A polymer according to claim 1, wherein said one or more β-dicarbonyl groups are selected from the group consisting of β-ketoester groups, β-diester groups, and β-diketone groups; said ionic group is selected from the group consisting of carboxyl groups, boric groups, phosphonic groups, and sulphonic groups; said crosslinking group is selected from the group consisting of epoxies, acrylates, methacrylates, alkenes, acrylamides, and vinyl ethers; m is a number having an average value between about 5 and 500; n is a number having an average value between about 10 and 500; p is a number having an average value between about 50 and about 400; and said polymer has a weight average molecular weight between 10,000 and 100,000.

* * * * *